United States Patent [19]

Vester et al.

[11] Patent Number: 5,287,853
[45] Date of Patent: Feb. 22, 1994

[54] ADAPTER CABLE FOR CONNECTING A PULSOXIMETRY SENSOR UNIT TO A MEDICAL MEASURING DEVICE

[75] Inventors: Joachim Vester, Aidlingen; Heinz Sommer, Boeblingen, both of Fed. Rep. of Germany

[73] Assignee: Hewlett-Packard Company, Palo Alto, Calif.

[21] Appl. No.: 989,115

[22] Filed: Dec. 11, 1992

[51] Int. Cl.$^5$ ............................................. A61B 5/00
[52] U.S. Cl. ..................................... 128/633; 356/41; 439/606
[58] Field of Search .................. 128/633–634, 128/664–667; 356/39–41; 439/638–639, 604, 606, 623

[56] References Cited

U.S. PATENT DOCUMENTS

| | | | |
|---|---|---|---|
| 4,446,715 | 5/1984 | Bailey | 128/667 X |
| 4,621,643 | 11/1986 | New, Jr. et al. | 356/41 X |
| 4,684,245 | 8/1987 | Goldring | 356/41 |
| 5,113,861 | 5/1992 | Rother | 356/41 X |
| 5,149,503 | 9/1992 | Kohno et al. | 356/41 X |

Primary Examiner—Angela D. Sykes
Attorney, Agent, or Firm—Perman & Green

[57] ABSTRACT

An adapter cable is used for connecting a pulsoximetry sensor unit to a medical measuring device. The pulsoximetry sensor unit comprises, among other components, two antiparallel-connected, light-emitting diodes, which are activated alternatingly by a pulse current source of the medical measuring device. Between said pulsoximetry sensor unit and said medical measuring device, a plurality of grounding lines extend within the adapter cable. In the case of a short circuit between one of the two supply lines of the antiparallel-connected, light-emitting elements and one of the grounding lines, the fault current is caused to flow in the grounding lines to a first node in accordance with the present invention, said first node being adapted to be connected to a reference potential of the medical measuring device via a first resistor. The voltage drop across said first resistor will cause firing of a thyristor structure, if a limit value is exceeded, provided that the instantaneous control phase of the pulse current source of the medical measuring device can cause an activation of a predetermined element of the two light-emitting elements. The triggered thyristor circuit will cause an activation of a switch, which will establish a shunt to the light-emitting elements.

9 Claims, 1 Drawing Sheet

ADAPTER CABLE FOR CONNECTING A PULSOXIMETRY SENSOR UNIT TO A MEDICAL MEASURING DEVICE

FIELD OF THE INVENTION

The present invention refers to the field of medical measuring devices which are capable of carrying out a non-invasive measurement of the oxygen saturation of hemoglobin in the blood of a patient.

More precisely, the subject matter of the present invention refers to an adapter cable, which is adapted to be connected to a pulsoximetry sensor unit on the one hand and to a medical measuring device for determining the oxygen saturation on the other.

DESCRIPTION OF THE PRIOR ART

For the purpose of measuring the oxygen saturation in the blood of a patient, a spectroscopic method of measurement, which is referred to a pulsoximetry, is nowadays normally used. This method of measurement is based on the finding that oxyhemoglobin is bright, whereas hemoglobin which is not laden with oxygen is optically dark. For determining the oxygen concentration in the blood of a part of the body supplied with pulsating blood, said part of the body is transilluminated alternatingly with light of a first wavelength and light of a second wavelength by means of two light-emitting elements emitting light of different wavelengths. The percent attenuation of the light passing through the respective transilluminated part of the body is detected by a common receiving diode for receiving said light having the first wavelength and said light having the second wavelength. The respective amplitudes of the received light of the first and second wavelengths pulsate corresponding to the pulsation of the blood between respective maximum and minimum amplitudes. The oxygen saturation $SpO_2$ can be calculated on the basis of these amplitudes of the received light of the first and second wavelengths.

Typically, the two light-emitting elements will be a red light-emitting diode as well as an infrared light-emitting diode. When red light-emitting diodes are produced, a wide spread of wavelengths is obtained. In order to prevent the pulsoximetry measuring result from being influenced by said spread of wavelengths, either the red light-emitting diodes will be selected such that they lie within a single wavelength range, or all the red light-emitting diodes used for the pulsoximetry sensors will be measured with respect to their wavelengths, the measured wavelength value being then coded. The coding will be effected by selecting a coding resistor whose resistance value indicates the wavelength of the red light-emitting diode. This coding resistor is additionally incorporated into or cast in the pulsoximetry sensor unit.

There are pulsoximetry sensor units produced by different manufacturers and having different connector components, and there are also associated medical measuring devices produced by different manufacturers and having different connector components. In order to be able to connect said pulsoximetry sensors produced by said different manufacturers and having said different connector components to an existent medical measuring device for measuring the oxygen concentration, an adapter cable will normally be used with the aid of which the contacts of the connector component of the pulsoximetry sensor can be associated in a suitable manner with the contacts of the connector component of the medical measuring device.

Specific structural designs of the pulsoximetry sensor unit, which are connected via an adapter cable to a medical measuring device for determining the oxygen saturation, already resulted in clinical mishaps caused by the malfunctions of the pulsoximetry sensor unit explained hereinbelow. The best possibility of explaining these malfunctions will be an explanation with respect to the figure enclosed, which shows, in addition to the adapter cable according to the present invention, a fundamentally unchanged medical measuring device and a fundamentally unchanged pulsoximetry sensor unit. The design of the known adapter cable partially to the design of the inventive cable shown in the only Fig. The prior art adapter cable connects by means of a first line a first sensor terminal T1 to a first measuring device terminal C1 and by means of a second line a second sensor terminal T2 to a second measuring device terminal C2. First and second light-emitting diodes LED 1, LED 2 lie, in an antiparallel connection, between said first and second sensor terminals T1, T2, said first light-emitting diode LED 1 emitting red light and said second light-emitting diode LED 2 emitting infrared light.

Both light-emitting diodes LED 1, LED 2 have applied thereto a square-wave, alternatingly positively and negatively polarized supply current through the medical measuring device at the first and second measuring device terminals. For this purpose, the medical measuring device includes an operational amplifier OP having an alternatingly positive and negative reference voltage applied thereto at its non-inverting input, the output of said operational amplifier OP being connected to the first measuring device terminal C1 and the inverting input thereof being connected to the second measuring device terminal C2, which is connected to ground via a current sensing resistor RM.

The pulsoximetry sensor unit comprises a photosensitive element in the form of a photodiode P as well as the wavelength coding resistor R2, which has already been mentioned and the resistance value of which is representative of the wavelength of the radiation emitted by the red, first light-emitting diode LED 1. In the case of the known adapter cable (not shown), the anode of the photodiode P, which communicates with the third sensor terminal, is connected via a line to the third measuring device terminal C3, which has connected thereto an $SpO_2$ measuring circuit for determining the oxygen saturation of the hemoglobin in the blood of the examined part of the body supplied with pulsating blood. In the case of the known adapter cable, this third line is the core of a coaxial line whose shield which will be referred to hereinafter as inner shield forms a grounding line between the fourth sensor terminal and a fourth measuring device terminal C4, which is connected to chassis ground. The wavelength coding resistor R2 is connected at the sixth sensor terminal to the fourth measuring device terminal C4 of the medical measuring device via a grounding line, said fourth measuring device terminal C4 being connected to ground of the device, as has already been mentioned. The other terminal T5 of the wavelength coding resistor R2 communicates via an additional signal line with the fifth measuring device terminal C5, which is connected to the input of a wavelength detection circuit, said wavelength detection circuit determining, on the basis of the resistance value of the wavelength coding resistor R2, the red wavelength of the first light-emitting diode LED 1 of the pulsoximetry sensor unit used and supplying this value to the SpO2 measuring circuit for the purpose of correcting or compensating the calculated oxygen saturation of the hemoglobin.

The adapter cable may additionally comprise a classification resistor R7 connected between a sixth measuring device terminal C6 and a seventh measuring device terminal C7, said sixth measuring device terminal being connected to chassis ground and said seventh measuring device terminal C7 communicating with a sensor class detection circuit. By means of the value of the thus measured resistance, the medical measuring device will be provided with information on the class or on the structural design of the respective sensor used. The whole, known adapter cable comprises a shield which will be referred to hereinafter as outer shield OS, which is also adapted to be connected to the fourth measuring device terminal C4, said fourth measuring device terminal C4 being connected to chassis ground.

The above-mentioned clinical mishap resulting from the use of this known adapter cable in the case of a malfunction of the sensor used, or in the case of a malfunction of the adapter cable used, will occur, if there is a short circuit between the second sensor terminal T2 and one of the three above-mentioned grounding lines, viz. the grounding line for connecting the sixth sensor terminal to the fourth measuring device terminal, the inner shield line or grounding line for connecting the fourth sensor terminal T4 to the fourth measuring device terminal C4, or the outer shield enclosing the adapter cable. In this case, the current sensing resistor RM will be short-circuited, via the adapter cable and via the pulsoximetry sensor used, to the ground of the medical measuring device employed, whereby the light-emitting diodes LED 1, LED 2 will be supplied with the highest power which can be outputted by the operational amplifier OP. This will result in direct heating of said light-emitting diodes LED 1, LED 2 and in burning of the patient's skin by the light-emitting diodes LED 1, LED 2 which is in contact with the patient's skin.

In principle, it would be imaginable to provide the medical measuring devices with a circuit which is able to recognize the above-described malfunction of the pulsoximetry sensors. In view of the fact that a large number of such medical measuring devices has already been delivered, this would, however, necessitate an expensive recalling action.

SUMMARY OF THE INVENTION

Hence, it is a main object of the present invention to provide an adapter cable by means of which burning of the patient's skin by the two light-emitting elements of the pulsoximetry sensor unit will be avoided even if, due to malfunctioning of the respective pulsoximetry sensor unit used, an undesirable short circuit occurs between one of the sensor terminals of the pulsoximetry sensor unit for supplying the light-emitting elements and one of the sensor terminals for the grounding lines.

The present invention additionally aims at providing an adapter cable, which is used for connecting a pulsoximetry sensor unit to a medical measuring device and which, in the case of an undesirable short circuit between a supply line of the light-emitting elements of the pulsoximetry sensor unit and a grounding line, will prevent the pulsoximetry sensor unit from having applied thereto an ecessively high current.

An additional object of the present invention is to be seen in the provision of an adapter cable, which is used for connecting a pulsoximetry sensor unit to a medical measuring device and which, if a case of short-circuit is erroneously detected between a supply line of the light-emitting elements and a grounding line, will deactivate the light-emitting element which is liable to overlaod only during one control cycle of said light-emitting element, whereas during the following control cycles it will automatically resupply energy to both light-emitting elements.

In accordance with a first aspect of the invention, this object is achieved by an adapter cable for connecting a pulsoximetry sensor unit to a medical measuring device,
said pulsoximetry sensor unit comprising two antiparallel-connected, light-emitting elements for emitting light of different wavelengths into a part of the body supplied with pulsating blood and a photosensitive element for receiving light which has been allowed to pass through said part of the body supplied with pulsating blood, and
said medical measuring device providing a pulsed supply signal, which supplies power to the light-emitting elements, and determining, on the basis of a signal produced by said photosensitive element, the oxygen saturation of the hemoglobin contained in the blood of the transilluminated part of the body,
wherein said adapter cable comprises the following features:
first and second lines for connecting the antiparallel-connected, light-emitting elements with supply terminals of the medical measuring device;
a third line for connecting one terminal of the photosensitive element to a measuring signal input of the medical measuring device;
a first grounding line for connecting the other terminal of the photosensitive element to a reference potential terminal of the measuring device;
an electronic switch means, which is connected to said first and second lines and which, when activated, forms a shunt to at least one of the light-emitting elements, and
a fault current detection circuit, which is provided for detecting the current flowing through the first grounding line and for activating the electronic switch means, if the current flowing through said first grounding line exceeds a limit value.

In accordance with a second aspect of the invention, this object is achieved by an adapter cable for connecting a pulsoximetry sensor unit to a medical measuring device,
said pulsoximetry sensor unit comprising two antiparallel-connected, light-emitting elements for emitting light of different wavelengths into a part of the body supplied with pulsating blood and a photosensitive element for receiving light which has been allowed to pass through said part of the body supplied with pulsating blood, and
said medical measuring device providing a pulsed supply signal, which supplies power to the light-emitting elements, and determining, on the basis of a signal produced by said photosensitive element, the oxygen saturation of the hemoglobin contained in the blood of the transilluminated part of the body,
wherein said adapter cable comprises the following features:

first and second lines for connecting the antiparallel-connected, light-emitting elements with supply terminals of the medical measuring device;

a third line for connecting one terminal of the photosensitive element to a measuring signal input of the medical measuring device;

a fourth line for connecting the other terminal of the photosensitive element to a first node;

a first resistor connecting the first node to a second node;

a fifth line for connecting the second node to a reference potential terminal of the medical measuring device;

an electronic switch means, which is connected to said first and/or second line(s) in such a way that, when said electronic switch means is activated, the flow of an inadmissibly high current through the light-emitting elements will be prevented, and a fault current detection circuit, which is connected to said first and second nodes on its input side and to said electronic switch means on its output side and which will respond to a voltage drop across the first resistor exceeding a limit value so as to activate said electronic switch means.

In accordance with a third aspect of the invention, this object is achieved by an adapter cable for connecting a pulsoximetry sensor unit to a medical measuring device, said pulsoximetry sensor unit comprising two antiparallel-connected, light-emitting elements for emitting light of different wavelengths into a part of the body supplied with pulsating blood, a photosensitive element for receiving light which has been allowed to pass through said part of the body supplied with pulsating blood, and a coding resistor whose resistance value is representative of the wavelength of the light emitted by one of said light-emitting elements, and said medical measuring device providing a pulsed supply signal, which supplies power to the light-emitting elements, and determining, on the basis of a signal produced by said photosensitive element, the oxygen saturation of the hemoglobin contained in the blood of the transilluminated part of the body, wherein said adapter cable comprises the following features:

first and second lines for connecting the antiparallel-connected, light-emitting elements with supply terminals of the medical measuring device;

a third line for connecting one terminal of the photosensitive element to a measuring signal input of the medical measuring device;

a first grounding line for connecting the other terminal of the photosensitive element to a first node;

a coding resistor connection line for connecting one terminal of the coding resistor to a coding resistor terminal of the measuring device;

a second grounding line for connecting the other terminal of the coding resistor to the first node;

a third grounding line constructed as an outer shield of the adapter cable and connected to the first node;

a first resistor connecting said first node to the second node;

a fifth line for connecting the second node to a reference potential terminal of the measuring device;

an electronic switch means connected to said first and second lines and forming, when activated, a shunt to the light-emitting elements; and a fault current detection circuit, which responds to a voltage drop across the first resistor exceeding a limit voltage, so as to activate said electronic switch means.

SHORT DESCRIPTION OF THE DRAWING

The only fig. shows a circuit diagram of the adapter cable according to the present invention together with a circuit diagram of the pulsoximetry sensor unit, which is known per se, and a block diagram of the medical measuring device, which is known per se and to which the adapter cable is adapted to be connected.

DESCRIPTION OF THE PREFERRED EMBODIMENT OF THE INVENTION

Figure 1:
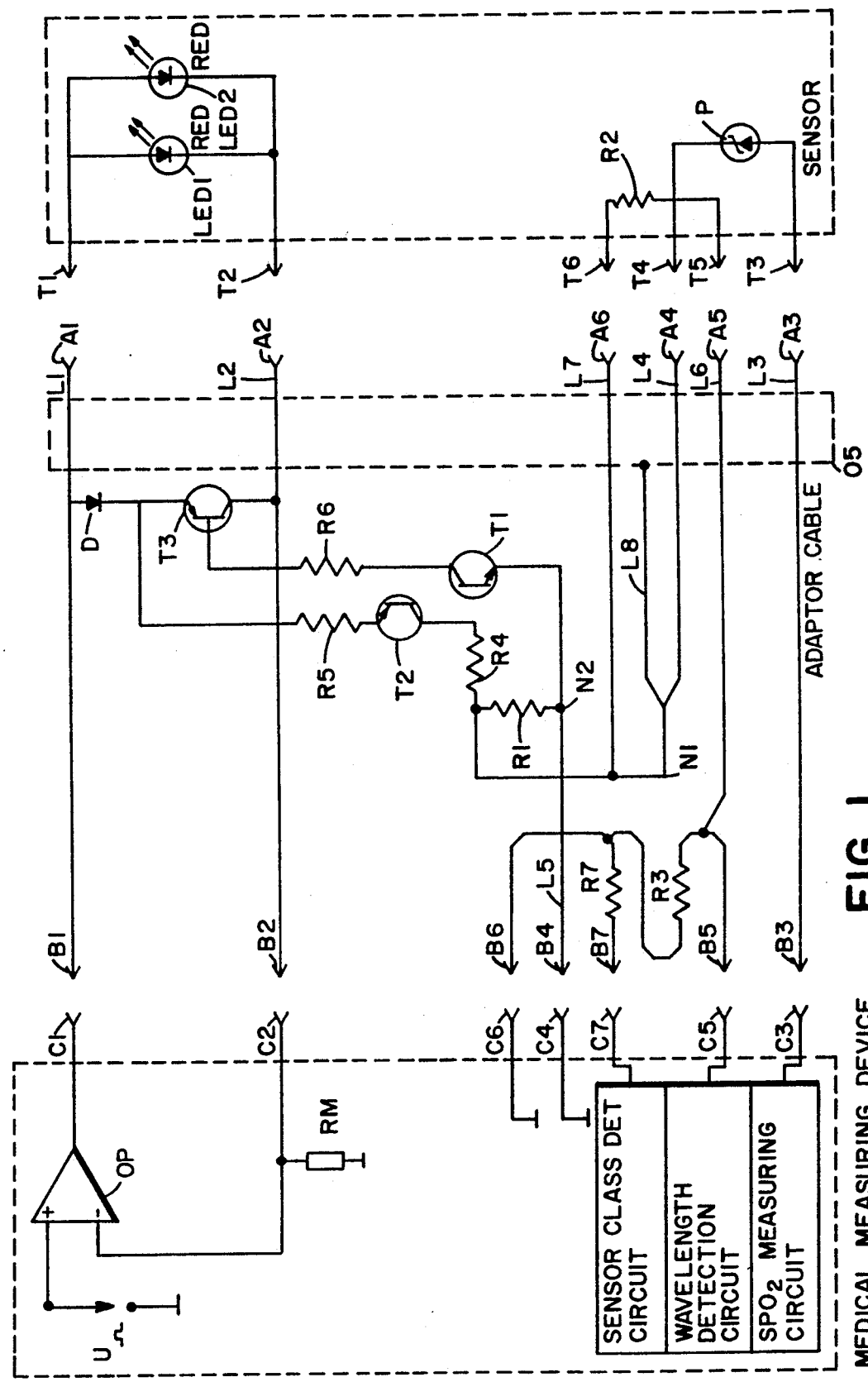

The structure of the pulsoximetry sensor unit, which is known per se and which is shown on the right-hand side of the only figure, as well as the structure of the medical measuring device, which is known per se and which is shown on the left-hand side of the only figure, has already been described in the explanation of the mode of operation of the known adapter cable. Hence, a renewed description of the pulsoximetry sensor unit as well as of the medical measuring device to which the adapter cable explained hereinbelow has to be connected can be dispensed with.

A first and a second line L1, L2 extend between a first and a second cable terminal A1, A2, respectively, located on the side of the sensor, and a first and a second cable terminal B1, B2, respectively, located on the side of the measuring device. At this point, reference is already made to the fact that, in the case of the preferred embodiment, the respective cable terminals A1 to A6 located on the side of the sensor and the first to sixth sensor terminals T1 to T6 are defined by matching elements of a connector located on the side of the sensor. Correspondingly, the first to sixth cable terminals B1 to B6 located on the side of the measuring device as well as the first to sixth measuring device terminals C1 to C6 are, in the case of the preferred embodiment, defined by contact elements of an additional connector, which is located on the side of the measuring device and which can, for example, be a Cannon connector.

The first and second lines L1, L2 serve to transmit the alternatingly positive and negative pulse current to the light-emitting elements LED 1, LED 2, said pulse current being supplied by the rectangular current source OP, RM located on the side of the measuring device.

A third line L3 extends between a third cable terminal A3 on the side of the sensor and a third cable terminal B3 on the side of the measuring device and serves to connect the anode of the photodiode P of the pulsoximetry sensor unit to the third measuring device terminal C3, which communicates with the input of the $SpO_2$ measuring circuit. A fourth line L4 connects the fourth cable terminal on the side of the sensor and, consequently, the cathode of the photodiode P to a first node N1 within the adapter cable. A sixth line connects the fifth cable terminal A5 on the side of the sensor to the fifth cable terminal B5 on the side of the measuring device, said fifth cable terminal B5 being, in turn, connected to the input of the wavelength detection circuit within the medical measuring device. The grounding line of the wavelength coding resistor R2, which is connected to the fifth sensor terminal, extends as a seventh line L7 from the sixth cable terminal A6 on the side of the sensor to the first node N1.

The whole adapter cable is enclosed by an outer shield OS connected to the first node N1 via an eighth line L8.

In the case of the preferred embodiment, the adapter cable comprises a coaxial cable whose inner core defines the third line L3 and whose inner shield defines the fourth line L4, which are used for establishing a connection to the photodiode P.

A fifth line L5 extends between the fourth cable terminal B4, which is located on the side of the measuring device and which is adapted to be connected to ground via the fourth measuring device terminal C4, and a second node N2 connected to the first node N1 through a first resistor R1. A sixth cable terminal B6, which is located on the side of the measuring device and which is adapted to be connected to ground via the sixth measuring device terminal C6, communicates with a seventh cable terminal B7, which is located on the side of the measuring device, via a classification resistor R7 whose resistance value can be detected by the medical measuring device with the aid of the sensor class detection circuit, whereby the medical device will obtain information on the type of pulsoximetry sensor used at the time in question.

The adapter cable comprises an electronic switch means, which is defined by the series connection of a diode D and of a third transistor T3, said series connection forming, when activated, a shunt to the red light-emitting diodes LED 1. In the case of fault currents, this electronic switch means D, T3 can be activated by a fault current detection circuit, which will be explained hereinbelow.

The fault current detection circuit comprises first and second transistors T1, T2 in thyristor connection, the emitter of the second transistor T2 being connected to a common node of the diode D and of the third transistor T3 via a fifth resistor. The cathode of the thyristor circuit is connected to the second node N2. The collector of the first transistor T1 is the anode of the thyristor. The first node N1 communicates via a fourth resistor with the base terminal of the first transistor of the thyristor circuit, whereas the base terminal of the second transistor T2 of the thyristor circuit communicates via a sixth resistor R6 with the base of the third transistor T3.

A compensating resistor R3 is positioned between the fifth cable terminal B5 on the side of the measuring device and the sixth cable terminal B6 on the side of the measuring device, said sixth cable terminal B6 being adapted to be connected to ground and, consequently, it is adapted to be connected in parallel with the series connection of the wavelength coding resistor R2 and of the first resistor R1.

As will be explained in detail hereinbelow, the first resistor R1 is used in the case of the disclosed embodiment of the adapter cable according to the present invention for the purpose of determining the current flowing through the grounding lines L4, L7, L8 to the first node N1. However, in view of the fact that this resistor is necessarily connected in series with the wavelength coding resistor R2 for the wavelength detection circuit, the value of said first resistor R1 will additively falsify the value of said wavelength coding resistor R2. In the case of the preferred embodiment, the first resistor R1 has a value of 26.1 ohm, and it lies generally in a range of values of from 5 to 50 ohm. Depending on the wavelength of the red, first light-emitting diode LED 1, the values of the wavelength coding resistor R2 lie between 6.04 kilo ohm and 9.76 kilo-ohm. Due to the parallel connection of the compensating resistor R3 having a value of preferably 2.61 mega-ohm, the measured values of the wavelength coding resistor R2 remain within predetermined tolerance windows, which are predetermined for the various values of R2 in the software of the control of the medical measuring device for the lambda detection circuit.

The person skilled in the art will recognize that any short circuit between the second line L2 and one of the grounding lines L4, L7, L8 will result in an increase of the current across the first resistor R1, whereby the voltage drop across this resistor R1 will be increased. When the pulse current source for controlling the anti-parallel light-emitting diodes LED 1, LED 2 is in the phase in the case of which the first diode LED 1 is activated, the corresponding activation of the first transistor T1 of the thyristor structure will result in firing of the thyristor, whereby the third transistor T3 will be through-connected and will thus prevent the flow of an inadmissibly high current through the first light-emitting diode LED 1; said inadmissibly high current would otherwise occur due to short circuiting of the current sensing resistor RM within the medical measuring device.

An erroneous ignition of the thyristor T1, T2 does not have any negative consequences in the case of the adapter cable connection according to the present invention, since the thyristor will be turned off during the subsequent infrared phase in the course of which the current flowing through the first and second lines L1, L2 will activate the second light-emitting diode LED 2. It follows that, in the case of the adapter cable connection according to the present invention, resetting of this shunt switch means can be dispensed with as well, such resetting being required e.g. in the case of power supply units including a crowbar as current switch unit.

In the case of the embodiment described, the sensor is provided with a wavelength coding resistor R2, which, is, consequently, equipped with a grounding line L7 of its own, said grounding line L7 being connected to the first node N1 in the case of the adapter cable according to the present invention. As has been described at the beginning, there are also pulsoximetry sensor units which do not require the use of a coding resistor because the red light-emitting diodes LED 1 of such pulsoximetry sensor units are selected with regard to their wavelength. In this case, it is not only the wavelength coding resistor R2 which can be dispensed with, but also the sixth line L6 as well as the second line L7, which is connected to the first node N1 in the case of the embodiment shown.

In the case of the embodiment described, the adapter cable has an outer shield OS. When low-demand methods of measurement are used, this shield can be dispensed with, and, in this case, the eighth line L8, which is used for connecting the outer shield OS to the first node N1, will no longer be necessary either.

In each case, the adapter cable comprises at least the grounding line L4 of the photodiode P so that at least this grounding line will have to be checked with respect to an excessivly high fault current according to the teaching of the present invention.

In the case of the preferred embodiment, the fault current is caused to flow across a first resistor R1 connected between the first and second nodes. If the voltage across this first resistor R1 exceeds a specific limit value, the thyristor circuit will fire during the "red phase", which is predetermined by the pulse current source OP, RM. It is, however, also possible to use other embodiments of a fault current detection circuit, which will respond to an excessively high fault current in at least one of the grounding lines comprising at least the grounding line of the photodiode.

In the case of the embodiment described, the electronic switch means is shown as a series connection consisting of a diode and of a transistor. Other switch means, which are adapted to produce in a controllable manner a shunt for the diode LED 1 when the fault current detection circuit responds, can be used as well. The diode D, which is connected in series with the third transistor T3, can be dispensed with, if the base-emitter reverse voltage of the third transistor can assume excessively high values in the case of the embodiment used.

Circuits which can be used instead of the thyristor circuit are not only other self-holding circuits, but, renouncing an increased protective effect, non-self-holding control circuits can be used as well.

We claim:

1. An adapter cable for connecting a pulsoximetry sensor unit to a medical measuring device,
    said pulsoximetry sensor unit comprising two antiparallel-connected, light-emitting elements for emitting light of different wavelengths into a part of the body supplied with pulsating blood and a photosensitive element for receiving light which has been allowed to pass through said part of the body supplied with pulsating blood, and
    said medical measuring device providing a pulsed supply signal, which supplies power to the light-emitting elements, and determining, on the basis of a signal produced by said photosensitive element, the oxygen saturation of the hemoglobin contained in the blood of the transilluminated part of the body,
    wherein said adapter cable comprises the following features;
        first and second lines for connecting the antiparallel-connected, light-emitting elements with supply terminals of the medical measuring device;
        a third line for connecting one terminal of the photosensitive element to a measuring signal input of the medical measuring device;
        a first grounding line for connecting another terminal of the photosensitive element to a reference potential terminal of the measuring device;
        an electronic switch means, which is connected to said first and second lines and which, when activated, forms a shunt to at least one of the light-emitting elements, and
        a fault current detection circuit, which detects current flowing through the first grounding line and for activating the electronic switch means, if the current flowing through said first grounding line exceeds a limit value.

2. An adapter cable for connecting a pulsoximetry sensor unit to a medical measuring device,
    said pulsoximetry sensor unit comprising two antiparallel-connected, light-emitting elements for emitting light of different wavelengths into a part of the body supplied with pulsating blood and a photosensitive element for receiving light which has been allowed to pass through said part of the body supplied with pulsating blood, and
    said medical measuring device providing a pulsed supply signal, which supplies power to the light-emitting elements, and determining, on the basis of a signal produced by said photosensitive element, the oxygen saturation of the hemoglobin contained in the blood of the transilluminated part of the body,
    wherein said adapter cable comprises the following features:
        first and second lines for connecting the antiparallel-connected, light-emitting elements with supply terminals of the medical measuring device;
        a third line for connecting one terminal of the photosensitive element to a measuring signal input of the medical measuring device;
        a fourth line for connecting another terminal of the photosensitive element to a first node;
        a first resistor connecting the first node to a second node;
        a fifth line for connecting the second node to a reference potential terminal of the medical measuring device;
        an electronic switch means, which is connected at least to one of said first or second lines in such a way that, when said electronic switch means is activated, a flow of limit-exceeding current through the light-emitting elements will be prevented, and
        a fault current detection circuit, having an input side connected to said first and second nodes and having an output side connected to said electronic switch means and responsive to a voltage drop across the first resistor exceeding a limit value so as to activate said electronic switch means.

3. An adapter cable according to claim 2, wherein the electronic switch means is connected to said first and second lines in parallel connection to the light-emitting elements so as to form, when activated, a shunt to at least one of said light-emitting elements.

4. An adapter cable according to claim 2, wherein said electronic switch means is a self-holding circuit, which responds to the voltage across the first resistor exceeding a limit value only if the medical measuring device applies to said first and second lines potentials suitable for activating a predetermined light-emitting element among the two light-emitting elements.

5. An adapter cable for connecting a pulsoximetry sensor unit to a medical measuring device,
    said pulsoximetry sensor unit comprising two antiparallel-connected, light-emitting elements for emitting light of different wavelengths into a part of the body supplied with pulsating blood, a photosensitive element for receiving light which has been allowed to pass through said part of the body supplied with pulsating blood, and a coding resistor whose resistance value is representative of the wavelength of the light emitted by one of said light-emitting elements, and
    said medical measuring device providing a pulsed supply signal, which supplies power to the light-emitting elements, and determining, on the basis of a signal produced by said photosensitive element, the oxygen saturation of the hemoglobin contained in the blood of the transilluminated part of the body,
    wherein said adapter cable comprises the following features:

first and second lines for connecting the antiparallel-connected, light-emitting elements with supply terminals of the medical measuring device;

a third line for connecting one terminal of the photosensitive element to a measuring signal input of the medical measuring device;

a first grounding line for connecting another terminal of the photosensitive element to a first node;

a coding resistor connection line for connecting one terminal of the coding resistor to a coding resistor terminal of the measuring device;

a second grounding line for connecting another terminal of the coding resistor to the first node;

a third grounding line constructed as an outer shield of the adapter cable and connected to the first node;

a first resistor connecting said first node to a second node;

a fifth line for connecting the second node to a reference potential terminal of the measuring device;

an electronic switch means connected to said first and second lines and forming, when activated, a shunt for at least one of the light-emitting elements; and a fault current detection circuit, which responds to a voltage drop across the first resistor exceeding a limit voltage, so as to activate said electronic switch means.

6. An adapter cable according to claim 5, comprising, in addition, a third resistor for compensation of a falsification of a coding resistor resistance value detected by the medical measuring device, said falsification being caused by the first resistor, wherein said third resistor has one terminal connected to the coding resistor connection line, another terminal of said third resistor adapted to be connected to the reference potential terminal of the medical measuring device.

7. An adapter cable according to claim 6, wherein said third resistor has a resistance value R3, which satisfies the following condition: 100 kilo-ohm $< R3 <$ 10 mega-ohm.

8. An adapter cable according to one of the claims 1, 2 or 5, wherein said electronic switch means is a series connection, which is connected between the first line and the second line and which comprises a diode and a transistor whose emitter-collector path is in series with said diode.

9. An adapter cable according to one of claims 1, 2 or 5, wherein the fault current detection circuit comprises two transistors in thyristor connection.

* * * * *